United States Patent [19]
Rich et al.

[11] Patent Number: 6,060,279
[45] Date of Patent: *May 9, 2000

[54] INTERFERON-α-INDUCED PROTEIN

[75] Inventors: Steven A. Rich; Paul S. Masters, both of Albany, N.Y.

[73] Assignee: Health Research, Incorporated, Albany, N.Y.

[ * ] Notice: This patent is subject to a terminal disclaimer.

[21] Appl. No.: 09/167,112

[22] Filed: Oct. 6, 1998

Related U.S. Application Data

[63] Continuation of application No. 08/668,289, Jun. 21, 1996, Pat. No. 5,834,235.

[51] Int. Cl.[7] .......................... C12P 21/06; C07H 21/02; C07H 21/04
[52] U.S. Cl. .................... 435/69.1; 435/252.33; 435/325; 435/320.1; 536/23.1; 536/23.5; 530/350
[58] Field of Search .................... 435/69.1, 325, 435/252.3, 252.33; 530/350, 351; 536/23.1, 23.5, 23.2, 23.4

[56] References Cited

U.S. PATENT DOCUMENTS 5,834,235  11/1998  Rich et al. ............................. 435/69.1

FOREIGN PATENT DOCUMENTS

WO 94/11505  5/1994  WIPO .

OTHER PUBLICATIONS

Rich, S.A., *J. of Clinical Investigation*, 95:219–226 (1995).
Rich et al., *J. of Biological Chemistry*, 271(2):1118–1126 (1996).
Moore et al., *J. of Biological Chemistry*, 262(18):8447–8450 (1987).
Oka et al., *Archives of Virology*, 115:63–73 (1990).
DeKeyser et al., *Clinical Immunology and Immunopathology*, 69(2):155–160 (1993).
Beresini et al., *J. of Immunology*, 140:485–493 (1988).
Gustafsson et al., *J. of Immunology*, 129:1952–1959 (1982).
Hooper, W.C., *Blood, Blood Products, and HIV*, 2d Ed., pp. 101–116, Chapman & Hall Medical, New York (1994).
Leanderson et al., *EMBO J.*, 1(12):1505–1511 (1982).
Sen. G.C. and Ransohoff, R.M., *Adv. Virus Res.*, 42:57–102 (1993).
Staeheli, P., *Adv. Virus Res.*, 38:147–200 (1990).
GenBank sequence number T54916 (Feb. 8, 1995).
Miyamoto, M., et al., *Cell* 54:903–913 (1988).
Gould, S.J., et al., *Proc Natl Acad Sci USA* 86:1934–1938 (1989).
Sczakiel, G. and Nedbal, W., *Trends in Microbiol.* 3:213–217 (1995).

*Primary Examiner*—Ponnathapu Achutamurthy
*Assistant Examiner*—Nashaat T. Nashed
*Attorney, Agent, or Firm*—Braman & Rogalskyj, LLP

[57] ABSTRACT

The present invention is directed to an isolated nucleic acid molecule encoding an interferon-α-induced protein, particularly the protein designated p36. Expression vectors and host cells comprising the nucleic acid molecule are also provided, as well as methods for increasing or decreasing the expression of the interferon-α-induced protein in host cells. DNA oligomers and antibodies specific for interferon-α-induced protein are provided, each of which can be used to detect interferon-α-induced protein in a sample. Methods for diagnosing immunodeficiency and autoimmune disease in an individual and methods for detecting the presence or past existence of lupus inclusions or interferon-α in a sample are also provided.

10 Claims, No Drawings

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 891 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
ATGACTAACC CAGAGTCTGC CGTACATGTG AAAATGATGC CAGAATTCCA GAAAAGTTCA        60

GTTCGAATCA AGAACCCTAC AAGAGTAGAA GAAATTATCT GTGGTCTTAT CAAAGGAGGA       120

GCTGCCAAAC TTCAGATAAT AACGGACTTT GATATGACAC TCAGTAGATT TTCATATAAA       180
```

```
GGGAAAAGAT GCCCAACATG TCATAATATC ATTGACAACT GTAAGCTGGT TACAGATGAA      240

TGTAGAAAAA AGTTATTGCA ACTAAAGGAA AAATATTACG CTATTGAAGT TGATCCTGTT      300

CTTACTGTAG AAGAGAAGTA CCCTTATATG GTGGAATGGT ATACTAAATC ACATGGTTTG      360

CTTGTTCAGC AAGCTTTACC AAAAGCTAAA CTTAAAGAAA TTGTGGCAGA ATCTGACGTT      420

ATGCTCAAAG AAGGATATGA GAATTTCTTT GATAAGCTCC AACAACATAG CATCCCCGTG      480

TTCATATTTT CGGCTGGAAT CGGCGATGTA CTAGAGGAAG TTATTCGTCA AGCTGGTGTT      540

TATCATCCCA ATGTCAAAGT TGTGTCCAAT TTTATGGATT TTGATGAAAC TGGGGTGCTC      600

AAAGGATTTA AAGGAGAACT AATTCATGTA TTTAACAAAC ATGATGGTGC CTTGAGGAAT      660

ACAGAATATT TCAATCAACT AAAAGACAAT AGTAACATAA TTCTTCTGGG AGACTCCCAA      720

GGAGACTTAA GAATGGCAGA TGGAGTGGCC AATGTTGAGC ACATTCTGAA AATTGGATAT      780

CTAAATGATA GAGTGGATGA GCTTTTAGAA AAGTACATGG ACTCTTATGA TATTGTTTTA      840

GTACAAGATG AATCATTAGA AGTAGCCAAC TCTATTTTAC AGAAGATTCT A              891

(2) INFORMATION FOR SEQ ID NO:2:

(i) SEQUENCE CHARACTERISTICS:
        (A) LENGTH: 297 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

Met Thr Asn Pro Glu Ser Ala Val His Val Lys Met Met Pro Glu Phe
1               5                  10                  15

Gln Lys Ser Ser Val Arg Ile Lys Asn Pro Thr Arg Val Glu Glu Ile
            20                  25                  30

Ile Cys Gly Leu Ile Lys Gly Gly Ala Ala Lys Leu Gln Ile Ile Thr
        35                  40                  45

Asp Phe Asp Met Thr Leu Ser Arg Phe Ser Tyr Lys Gly Lys Arg Cys
    50                  55                  60

Pro Thr Cys His Asn Ile Ile Asp Asn Cys Lys Leu Val Thr Asp Glu
65                  70                  75                  80

Cys Arg Lys Lys Leu Leu Gln Leu Lys Glu Lys Tyr Tyr Ala Ile Glu
                85                  90                  95

Val Asp Pro Val Leu Thr Val Glu Glu Lys Tyr Pro Tyr Met Val Glu
            100                 105                 110

Trp Tyr Thr Lys Ser His Gly Leu Leu Val Gln Gln Ala Leu Pro Lys
        115                 120                 125

Ala Lys Leu Lys Glu Ile Val Ala Glu Ser Asp Val Met Leu Lys Glu
130                 135                 140

Gly Tyr Glu Asn Phe Phe Asp Lys Leu Gln Gln His Ser Ile Pro Val
145                 150                 155                 160

Phe Ile Phe Ser Ala Gly Ile Gly Asp Val Leu Glu Glu Val Ile Arg
                165                 170                 175

Gln Ala Gly Val Tyr His Pro Asn Val Lys Val Ser Asn Phe Met
            180                 185                 190

Asp Phe Asp Glu Thr Gly Val Leu Lys Gly Phe Lys Gly Glu Leu Ile
        195                 200                 205

His Val Phe Asn Lys His Asp Gly Ala Leu Arg Asn Thr Glu Tyr Phe
    210                 215                 220
```

```
Asn Gln Leu Lys Asp Asn Ser Asn Ile Ile Leu Leu Gly Asp Ser Gln
225                 230                 235                 240

Gly Asp Leu Arg Met Ala Asp Gly Val Ala Asn Val Glu His Ile Leu
            245                 250                 255

Lys Ile Gly Tyr Leu Asn Asp Arg Val Asp Glu Leu Leu Glu Lys Tyr
                260                 265                 270

Met Asp Ser Tyr Asp Ile Val Leu Val Gln Asp Glu Ser Leu Glu Val
            275                 280                 285

Ala Asn Ser Ile Leu Gln Lys Ile Leu
    290                 295
```

(2) INFORMATION FOR SEQ ID NO:3:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

```
Leu Gln Ile Ile Thr Asp Phe Asp Met Thr Leu Ser Lys
1               5                   10
```

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

```
Met Ala Asp Gly Val Ala Asn Val Glu His Ile Leu Lys
1               5                   10
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

```
Val Val Ser Asn Phe Met Asp Phe Asp Glu Thr Gly Val Leu Lys
1               5                   10                  15
```

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
Asp Asn Ser Asn Ile Ile Leu Leu Gly Asp Ser Gln Gly Asp Leu Arg
1               5                   10                  15
```

(2) INFORMATION FOR SEQ ID NO:7:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

```
Tyr Tyr Ala Ile Glu Val Asp Pro Val Leu Thr Val Glu Gln Lys Tyr
1               5                   10                  15
Pro
```

(2) INFORMATION FOR SEQ ID NO:8:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

```
Tyr Met Asp Ser Tyr Asp Ile Val Leu Val Gln Asp Glu Ser Leu Glu
1               5                   10                  15
Val Ala Arg
```

(2) INFORMATION FOR SEQ ID NO:9:

(i) SEQUENCE CHARACTERISTICS:
        (A) LENGTH: 1541 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CTTTTGCTGG TGTAGCTCGT CCGGTTACCT TCAGGAAGAT TGGATAACAA GAAATGACTA     60
ACCCAGAGTC TGCCGTACAT GTGAAAATGA TGCCAGAATT CCAGAAAAGT TCAGTTCGAA    120
TCAAGAACCC TACAAGAGTA AAGAAATTA TCTGTGGTCT TATCAAAGGA GGAGCTGCCA     180
AACTTCAGAT AATAACGGAC TTTGATATGA CACTCAGTAG ATTTTCATAT AAAGGGAAAA    240
GATGCCCAAC ATGTCATAAT ATCATTGACA ACTGTAAGCT GGTTACAGAT GAATGTAGAA    300
AAAAGTTATT GCAACTAAAG GAAAAATATT ACGCTATTGA AGTTGATCCT GTTCTTACTG    360
TAGAAGAGAA GTACCCTTAT ATGGTGGAAT GGTATACTAA ATCACATGGT TTGCTTGTTC    420
AGCAAGCTTT ACCAAAAGCT AAACTTAAAG AAATTGTGGC AGAATCTGAC GTTATGCTCA    480
AAGAAGGATA TGAGAATTTC TTTGATAAGC TCCAACAACA TAGCATCCCC GTGTTCATAT    540
TTTCGGCTGG AATCGGCGAT GTACTAGAGG AAGTTATTCG TCAAGCTGGT GTTTATCATC    600
CCAATGTCAA AGTTGTGTCC AATTTTATGG ATTTTGATGA AACTGGGGTG CTCAAAGGAT    660
TTAAGGAGA ACTAATTCAT GTATTTAACA AACATGATGG TGCCTTGAGG AATACAGAAT     720
ATTTCAATCA ACTAAAAGAC AATAGTAACA TAATTCTTCT GGGAGACTCC CAAGGAGACT    780
TAAGAATGGC AGATGGAGTG GCCAATGTTG AGCACATTCT GAAAATTGGA TATCTAAATG    840
ATAGAGTGGA TGAGCTTTTA GAAAAGTACA TGGACTCTTA TGATATTGTT TTAGTACAAG    900
```

-continued

```
ATGAATCATT AGAAGTAGCC AACTCTATTT TACAGAAGAT TCTATAACAG CATTCTCCAA      960

GAAGACCTCT CTCCTGTGGG TGCAATTGAA CTGTTCATCC GTTCATCTTG CTGAGAGACT     1020

TATTTATAAT ATATCCTTAC TCTCGAAGTG TTCCCTTTGT ATAACTGAAG TATTTTCAGA     1080

TATGGTGAAT GCATTGACTG GAGCTCCTTT TCTCCACCTC TCTCAACACA CATCCTCACC     1140

GTATCTTTTA ACCCATTTAA AAAAAAAAAA GCTAAAATTA GAAAAATAAC TCCCTACTTT     1200

TCCAAAGTGA ATTTTGTAGT TTAATGTTAT CATGCAGCTT TTGAGGAGTC TTTTACACTG     1260

GGAAAGTTTG TAGAAATTTT AAAATAAGTT TTATGAAATG GTGAAATAAT ATGCATGATT     1320

TTAAGTATTG CCATTTTTGT AATTTGGGTT ATTATGCTGA TGGTATCACC ATCTCTTGAA     1380

ATTGTGTTAG GTTTGGTTAT TTTGTCTGGG GAAAAAATAT TTACTGGAAA AGACTAGCAG     1440

TTAGTGTTGG AAAAACCTGG TGGTGTTTAC AATGTTGCTA ATCATTACAA AACATTCTAT     1500

ATTGAAGCAC TGATAATAAA TATGAAATGC AAAACCTTTT T                        1541
```

INTERFERON-α-INDUCED PROTEIN

This application is a continuation of U.S. Ser. No. 08/668,289, filed Jun. 21, 1996, U.S. Pat. No. 5,834,235.

The subject matter of this application was made with support from the United States Government under Grant AR 41619 from the National Institutes of Health.

FIELD OF THE INVENTION

The present invention relates generally to an interferon-α-induced protein and, more particularly, to nucleic acid molecules encoding an interferon-α-induced protein and uses thereof.

BACKGROUND OF THE INVENTION

Throughout this application various publications are referenced, many in parenthesis. Full citations for these publications are provided at the end of the Detailed Description of the Invention. The disclosures of these publications in their entireties are hereby incorporated by reference in this application.

Interferons ("IFNs") are a family of cytokines (Henco et al. 1985; Dron and Tovey 1992) with a variety of biological activities (Pestka et al. 1987 and Baron et al. 1992). They are named for their originally discovered activity of interfering with the infection of cells by virus (Issacs and Lindenmann 1957). Their use in the treatment of tumors is derived primarily from their ability to inhibit the growth of cells and to modulate cellular differentiation (Gutterman 1994). They are also known to affect every component of the immune system (Dianzani 1992), and long-term IFN-α therapy has induced systemic autoimmunity (Tolaymat et al. 1992, Wandl et al. 1992, Skurkovich et al. 1993, Stewart et al 1993, Paul and Seder 1994, and Schattner 1994). The mechanism for this is, in part, mediated through the induction of other cytokines that also act to modulate the immune system (Hooper 1994).

The biological activities of IFNs and other cytokines are mediated through binding and activation of specific receptors of the cytokine receptor superfamily (Ihle and Kerr 1995). The cell response occurs by the phosphorylation of selected signal transducers and activators of transcription ("STAT") proteins by specific Jak kinases (Heim et al. 1995). The phosphorylated proteins form complexes, which migrate to the nucleus, bind to a specific promoter (interferon-stimulated response element for IFN-αs), and activate the corresponding genes. Specificity of cell activation is attributed to the particular STAT proteins that are phosphorylated. These are determined by the STAT's particular phosphotyrosine-binding domain for the receptor rather than by the Jak kinases that associate with the receptor (Heim et al. 1995). Many cytokines use the same STAT proteins in their intracellular activation pathways. This may suggest that individually or in combination cytokines may activate some of the same genes to induce at least some of the same proteins.

The most studied IFN-induced proteins, such as Mx, PI/eIF-2α protein kinase, and 2'5'-oligo(A) synthetases, are those believed to be necessary for establishing an antiviral state (Staeheli 1990 and Sen and Ransohoff 1993). Cytokine tumor necrosis factor is also known to be induced by IFN-α (Hooper 1994). Most other induced proteins have been identified on two-dimensional gels only as protein spots (Gustafsson et al. 1982, Leanderson et al. 1982, and Beresini et al. 1988). Their functions and biological significances are unknown. Many of these proteins are synthesized constitutively at low levels, and they are enhanced in response to both α- and γ-IFNs (Staeheli 1990, Sen and Ransohoff 1993, and Beresini et al. 1988).

Lupus inclusions ("LI") (also called tubuloreticular structures or tubuloreticular inclusions) are IFN-α-induced (Rich 1981) abnormal cytoplasmic structures of unknown function that resemble myxovirus by ultramorphology (see, for example FIG. 1 of Gyorkey et al. 1969). They are membrane delimited complexes of tubular structures, 20 to 28 nm in diameter, and are characterized by their unique ultrastructural appearance. LI are composed of ribonucleoprotein and membrane complexes with carbohydrate and no DNA. They form in a restricted region of the endoplasmic reticulum ("ER") that makes contact with adjacent regions of the outer nuclear envelope and the Golgi apparatus (Rich et al. 1992). As indicated above, the function of LI is not known. However, the ER location of LI suggests that they may affect the established ER functions of membrane biogenesis, the trafficking of proteins to the plasma membrane or to cytoplasmic vesicles, or the processing of proteins for secretion.

LI formation in endothelial and mononuclear cells is a prognostic marker for disease progression in individuals with acquired immune deficiency syndrome ("AIDS") (Feremans et al. 1988, Orenstein et al. 1985, and Sidhu 1985), and their incidence reflects the disease activities of individuals with systemic lupus erythematosus ("SLE") (Rich et al. 1986). These structures are not detected in the cells of healthy individuals (Rich et al. 1986). An unusual acid-labile IFN-α is present continuously in the circulation of individuals with SLE and AIDS (De Stefano et al. 1982 and Preble et al. 1982). This is in contrast to a typical viral infection, in which IFN-α is produced as a burst for a 24 h period only. The unusual acid-labile IFN-α in sera from individuals with SLE and AIDS has an extraordinary ability to induce LI (Rich et al 1986 and Rich and Owens 1984). LI are known to be products of normal cells abnormally stimulated with IFN-α because peripheral blood mononuclear cells from healthy adult Red Cross blood donors (Rich et al. 1983) and umbilical-cord bloods from routine births (Rich and Gibbons 1990) form LI when cultured with IFN-α.

Because of their association with immunodeficiency and autoimmune diseases, such as SLE and AIDS, LI or LI associated proteins have been investigated extensively for monitoring the progression of these diseases and the effectiveness of treatment regimens as well as for therapeutic activity. However, detection of LI is complicated by their small size and by the need to detect their presence visually. As to proteins uniquely associated with LI, though some are presently known, they have not been characterized in terms of their amino acid and nucleotide sequence. Because the nucleotide sequence encoding these proteins has heretofore been unknown, isolation of these proteins in useful quantities has not been achieved, and the use of the knowledge of such sequence data has not been possible.

A need exists, therefore, for the determination of the nucleotide and amino acid sequences of proteins induced by interferon-α or uniquely associated with LI. The present invention is directed to meeting this need.

SUMMARY OF THE INVENTION

The present invention relates to isolated nucleic acid molecules encoding an interferon-α-induced protein, as well as to antisense molecules and ribozymes derived therefrom.

The isolated nucleic acid molecules of the invention can be inserted into suitable expression vectors and/or host cells. Expression of the nucleic acid molecules encoding the interferon-α-induced protein results in production of interferon-α-induced protein in a host cell. Expression of the antisense nucleic acid molecules in a host cell or introduction of the ribozymes into a host cell results in decreased expression of the interferon-α-induced protein.

Further provided is an isolated nucleic acid molecule encoding an interferon-α-induced protein, wherein the nucleic acid molecule encodes a first amino acid sequence having at least 90% amino acid identity to a second amino acid sequence. The second amino acid sequence is, in a preferred embodiment, SEQ ID NO: 2.

The invention further provides a DNA oligomer capable of hybridizing to a nucleic acid molecule encoding an interferon-α-induced protein. The DNA oligomer can be used in a method of detecting presence of a nucleic acid molecule encoding an interferon-α-induced protein in a sample, which method is also provided by the subject invention. The invention also provides an antibody or fragment thereof specific for an interferon-α-induced protein encoded by the nucleic acid molecule of the subject invention. The antibody or fragment thereof can also be used in a method of detecting the presence of an interferon-α-induced protein in a sample, which method is also provided by the subject invention.

The invention further provides a method for detecting presence or prior existence of interferon-α in a sample, by detecting presence of an interferon-α induced protein in the sample. Further provided is a method for detecting presence or past existence of lupus inclusions in a sample, by detecting presence of an interferon-α-induced protein in the sample.

In another aspect, the present invention relates to methods for diagnosing immunodeficiency or autoimmune disease in an individual. In one embodiment, the method includes providing a sample of mononuclear or endothelial cells from the individual and detecting presence of an interferon-α-induced protein in the sample. In a further embodiment, the method includes inducing a sample of Raji or Daudi cells with a serum sample from the individual, and detecting the presence of an interferon-α-induced protein in the induced Raji or Daudi cells sample.

DETAILED DESCRIPTION OF THE INVENTION

As used herein, the term "isolated" when used in conjunction with a nucleic acid molecule refers to: 1) a nucleic acid molecule which has been separated from an organism or cell in a substantially purified form (i.e. substantially free of other substances originating from that organism or cell), or 2) a nucleic acid molecule having the same nucleotide sequence but not necessarily separated from the organism (i.e. synthesized nucleic acid molecules).

As further used herein, the terms "corresponding to" or "having" or "as shown in" or "consisting of" when used in conjunction with a SEQ ID NO for a nucleotide sequence refer to a nucleotide sequence which is substantially the same nucleotide sequence, or derivatives thereof (such as deletion and hybrid variants thereof, splice variants thereof, etc.). Nucleotide additions, deletions, and/or substitutions, such as those which do not affect the translation of the DNA molecule, are within the scope of a nucleotide sequence corresponding to or having or as shown in or consisting of a particular nucleotide sequence (i.e. the amino acid sequence encoded thereby remains the same). Such additions, deletions, and/or substitutions can be, for example, the result of point mutations made according to methods known to those skilled in the art. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting interferon-α-induced protein. These are also within the scope of a nucleotide sequence corresponding to or having or as shown in or consisting of a particular nucleotide sequence.

Similarly, the term "corresponding to" or "having" or "as shown in" or "consisting of" when used in conjunction with a SEQ ID NO for an amino acid sequence refers to an amino acid sequence which is substantially the same amino acid sequence or derivatives thereof. Amino acid additions, deletions, and/or substitutions which do not negate the ability of the resulting protein to form a functional interferon-α-induced protein are within the scope of an amino acid sequence corresponding to or having or as shown in or consisting of a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, alanine, valine, leucine, isoleucine, glycine, cysteine, phenylalanine, tryptophan, methionine, and proline, all of which are nonpolar residues, are of the same type. Serine, threonine, tyrosine, asparagine, and glutamine, all of which are uncharged polar residues, are of the same type. Another type of residue is the positively charged (basic) polar amino acid residue, which includes histidine, lysine, and arginine. Aspartic acid and glutamic acid, both of which are negatively charged (acidic) polar amino acid residues, form yet another type of residue. Further descriptions of the concept of conservative substitutions are given by French and Robson 1983, Taylor 1986, and Bordo and Argos 1991.

As further used herein, the term "corresponding to" or "having" or "as shown in" or "consisting of" when used in conjunction with a SEQ ID NO for a nucleotide or amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified nucleotide or amino acids within the recited sequence. For example, those skilled in the art will readily understand that an adenine nucleotide could be replaced with a methyladenine, or a cytosine nucleotide could be replaced with a methylcytosine, if a methyl side chain is desirable. Nucleotide sequences having a given SEQ ID NO are intended to encompass nucleotide sequences containing these and like derivative or modified nucleotides, as well as cyclic variations. As a further example, those skilled in the art will readily understand that an asparagine residue could be replaced with an ethylasparagine if an ethyl side chain is desired, a lysine residue could be replaced with a hydroxylysine if an OH side chain is desired, or a valine residue could be replaced with a methylvaline if a methyl side chain is desired. Amino acid sequences having a given SEQ ID NO are intended to encompass amino acid sequences containing these and like derivative or modified amino acids, as well as cyclic variations. Cyclic, as used herein, also refers to cyclic versions of the derivative or modified nucleotides and amino acids.

With these definitions in mind, the subject invention provides an isolated nucleic acid molecule encoding an interferon-α-induced protein. The nucleic acid molecule can be deoxyribonucleic acid ("DNA") or ribonucleic acid ("RNA"), the latter including messenger RNA ("mRNA"). The nucleic acid can be genomic or recombinant, biologically isolated or synthetic.

The DNA molecule can be a cDNA molecule, which is a DNA copy of an mRNA encoding the interferon-α-induced protein.

In one embodiment, the interferon-α-induced protein has a molecular mass of about 36 kDa. This human interferon-α-induced protein is encoded by the nucleotide sequence as shown in SEQ ID NO: 1 and has an amino acid sequence as shown in SEQ ID NO: 2.

The invention also provides an antisense nucleic acid molecule that is complementary to at least a portion of the mRNA encoding the interferon-α-induced protein. Antisense nucleic acid molecules can be RNA or single-stranded DNA, and can be complementary to the entire mRNA molecule encoding the interferon-α-induced protein (i.e. of the same nucleotide length as the entire molecule). It may be desirable, however, to work with a shorter molecule. In this instance, the antisense molecule can be complementary to a portion of the entire mRNA molecule encoding the interferon-α-induced protein. These shorter antisense molecules are capable of hybridizing to the mRNA encoding the entire molecule, and preferably consist of at least twenty nucleotides. These antisense molecules can be used to reduce levels of interferon-α-induced protein, by introducing into cells an RNA or single-stranded DNA molecule that is complementary to at least a portion of the mRNA of the interferon-α-induced protein (i.e. by introducing an antisense molecule). The antisense molecule can base-pair with the mRNA of the interferon-α-induced protein, preventing translation of the mRNA into protein. Thus, an antisense molecule to the interferon-α-induced protein can prevent translation of mRNA encoding the interferon-α-induced protein into a functional interferon-α-induced protein.

More particularly, an antisense molecule complementary to at least a portion of mRNA encoding an interferon-α-induced protein can be used to decrease expression of a functional interferon-α-induced protein. A cell with a first level of expression of a functional interferon-α-induced protein is selected, and then the antisense molecule is introduced into the cell. The antisense molecule blocks expression of functional interferon-α-induced protein, resulting in a second level of expression of a functional interferon-α-induced protein in the cell. The second level is less than the initial first level.

Antisense molecules can be introduced into cells by any suitable means. In one embodiment, the antisense RNA molecule is injected directly into the cellular cytoplasm, where the RNA interferes with translation. A vector may also be used for introduction of the antisense molecule into a cell. Such vectors include various plasmid and viral vectors. For a general discussion of antisense molecules and their use, see Han et al. 1991 and Rossi 1995. Suitable cells for introduction of antisense molecules include tumor cells, particularly those where interferon-α is typically expressed or where lupus inclusions typically form. In these cells, increased levels of interferon-α-induced protein are associated with the formation of lupus inclusions which are, in turn, associated with immunodeficiency and autoimmune diseases such as AIDS and lupus erythematosus, or autoimmune conditions arising from interferon-α treatment.

The invention further provides a special category of antisense RNA molecules, known as ribozymes, having recognition sequences complementary to a portion of the mRNA encoding the interferon-α-induced protein. Ribozymes not only complex with target sequences via complementary antisense sequences but also catalyze the hydrolysis, or cleavage, of the template mRNA molecule. Examples, which are not intended to be limiting, of suitable regions of the mRNA template to be targeted by ribozymes are any regions unique to the interferon-α-induced protein such that only the mRNA encoding interferon-α-induced protein is cleaved. Such unique regions can be identified by comparision of nucleotide sequences.

Expression of a ribozyme in a cell can inhibit gene expression (such as the expression of an interferon-α-induced protein). More particularly, a ribozyme having a recognition sequence complementary to a region of a mRNA encoding an interferon-α-induced protein can be used to decrease expression of interferon-α-induced protein. A cell with a first level of expression of interferon-α-induced protein is selected, and then the ribozyme is introduced into the cell. The ribozyme in the cell decreases expression of interferon-α-induced protein in the cell, because mRNA encoding the interferon-α-induced protein is cleaved and cannot be translated.

Ribozymes can be introduced into cells by any suitable means. In one embodiment, the ribozyme is injected directly into the cellular cytoplasm, where the ribozyme cleaves the mRNA and thereby interferes with translation. A vector may be used for introduction of the ribozyme into a cell. Such vectors include various plasmid and viral vectors. As the skilled practitioner will note, the DNA encoding the ribozyme does not need to be "incorporated" into the genome of the host cell; it could be expressed in a host cell infected by a viral vector, with the vector expressing the ribozyme, for instance. For a general discussion of ribozymes and their use, see Sarver et al. 1990, Chrisey et al. 1991, Rossi et al. 1992, and Christoffersen et al. 1995. Suitable cells for introduction of ribozymes according to the subject invention include tumor cells, particularly those where interferon-α is typically expressed or where lupus inclusions typically form. In these cells, increased levels of interferon-α-induced protein are associated with the formation of lupus inclusions which are, in turn, associated with immunodeficiency and autoimmune diseases such as AIDS and lupus erythematosus, or autoimmune conditions arising from interferon-α treatment.

The nucleic acid molecules of the subject invention can be expressed in suitable host cells using conventional techniques. Any suitable host and/or vector system can be used to express the interferon-α-induced protein. For in vitro expression, bacterial hosts (for example, *Escherichia coli*) and mammalian hosts (for example, Hela cells, Cv-1 cells, COS cells) are preferred. Expression of the interferon-α-induced protein may be desirable to obtain amounts of the protein for study and/or research purposes, as well as for therapy for virus infections, cancer, and other diseases for which cytokines, in particular interferon-α, have been identified as useful.

Techniques for introducing the nucleic acid molecules into the host cells may involve the use of expression vectors which comprise the nucleic acid molecules. These expression vectors (such as plasmids and viruses; viruses including bacteriophage) can then be used to introduce the nucleic acid molecules into suitable host cells. For example, DNA encoding the interferon-α-induced protein can be injected into the nucleus of a host cell or transformed into the host cell using a suitable vector, or mRNA encoding the interferon-α-induced protein can be injected directly into the host cell, in order to obtain expression of interferon-α-induced protein in the host cell.

Various methods are known in the art for introducing nucleic acid molecules into host cells. One method is microinjection, in which DNA is injected directly into the nucleus of cells through fine glass needles (or RNA is injected directly into the cytoplasm of cells). Alternatively, DNA can be incubated with an inert carbohydrate polymer (e.g. dextran) to which a positively charged chemical group (e.g. diethylaminoethyl ("DEAE")) has been coupled. The DNA sticks to the DEAE-dextran via its negatively charged phosphate groups. These large DNA-containing particles, in turn, stick to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite 1988, Shigekawa and Dower 1988, Capecchi 1980, and Klein et al. 1987.

Further methods for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. For a review of baculovirus vectors, see Miller 1989. Various viral vectors have also been used to transform mammalian cells, such as vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al. (1989).

Host cells into which the nucleic acid encoding the interferon-α-induced protein has been introduced can be used to produce (i.e. to functionally express) the interferon-α-induced protein.

Having identified the nucleic acid molecules encoding interferon-α-induced protein and methods for increasing or decreasing expression of the interferon-α-induced protein encoded thereby, the nucleic acid molecules of the subject invention can be used either as probes or for the design of primers to obtain DNA encoding other homologous interferon-α-induced proteins by either cloning and colony/plaque hybridization or amplification using the polymerase chain reaction ("PCR").

Specific probes derived from SEQ ID NO 1 can be employed to identify colonies or plaques containing cloned DNA encoding a member of the interferon-α-induced protein family using known methods (see Sambrook et al. 1989). One skilled in the art will recognize that by employing such probes under high stringency conditions (for example, hybridization at 42° C. with 5X SSPC and 50% formamide, washing at 50–65° C. with 0.5X SSPC), sequences having regions which are greater than 90% homologous or identical to the probe can be obtained. Sequences with lower percent homology or identity to the probe, which also encode a member of the interferon-α-induced protein family, can be obtained by lowering the stringency of hybridization and washing (e.g., by reducing the hybridization and wash temperatures or reducing the amount of formamide employed).

More particularly, in one embodiment, the method comprises selection of a DNA molecule encoding an interferon-α-induced protein, or a fragment thereof, the DNA molecule having a nucleotide sequence as shown in SEQ ID NO: 1, and designing an oligonucleotide probe for interferon-α-induced protein based on SEQ ID NO: 1. A genomic or cDNA library of an organism is then probed with the oligonucleotide probe, and clones are obtained from the library that are recognized by the oligonucleotide probe so as to obtain DNA encoding proteins that are homologous to the interferon-α-induced protein.

Specific primers derived from SEQ ID NO: 1 can be used in PCR to amplify a DNA sequence encoding a member of the interferon-α-induced protein family using known methods (see Innis et al. 1990). One skilled in the art will recognize that by employing such primers under high stringency conditions (for example, annealing at 50–60° C., depending on the length and specific nucleotide content of the primers employed), sequences having regions greater than 75% homologous or identical to the primers will be amplified.

More particularly, in a further embodiment, the method comprises selection of a DNA molecule encoding interferon-α-induced protein or a fragment thereof, the DNA molecule having a nucleotide sequence as shown in SEQ ID NO: 1, designing degenerate oligonucleotide primers based on regions of SEQ ID NO: 1, and employing such primers in the polymerase chain reaction using as a template a DNA sample to be screened for the presence of interferon-α-induced protein-encoding sequences. The resulting PCR products can be isolated and sequenced to identify DNA fragments that encode polypeptide sequences corresponding to the targeted region of interferon-α-induced protein.

Various modifications of the nucleic acid and amino acid sequences disclosed herein are covered by the subject invention. These varied sequences still encode a functional interferon-α-induced protein. The invention thus further provides an isolated nucleic acid molecule encoding an interferon-α-induced protein, the nucleic acid molecule encoding a first amino acid sequence having at least 90% amino acid identity to a second amino acid sequence, the second amino acid being as shown in SEQ ID NO: 2.

The invention further provides an isolated DNA oligomer capable of hybridizing to the nucleic acid molecule encoding interferon-α-induced protein according to the subject invention. Such oligomers can be used as probes in a method of detecting the presence of nucleic acid molecules encoding interferon-α-induced protein in a sample. More particularly, a sample can be contacted with the DNA oligomer, and the DNA oligomer will hybridize to any nucleic acid encoding interferon-α-induced protein present in the sample, forming a complex therewith. The complex can then be detected, thereby detecting presence of nucleic acid molecules encoding interferon-α-induced protein in the sample.

The complex can be detected using methods known in the art. Preferably, the DNA oligomer is labeled with a detectable marker so that detection of the marker after the DNA oligomer hybridizes to nucleic acid sequences for the interferon-α-induced protein or closely related proteins in the sample (wherein non-hybridized DNA oligomer has been washed away) is detection of the complex. Detection of the complex indicates the presence of interferon-α-induced protein in the sample. As will be readily apparent to those skilled in the art, such a method could also be used quantitatively to assess the amount of interferon-α-induced protein in a sample. Such a quantitative method could be especially useful in samples of cells wherein interferon-α is typically expressed or wherein lupus inclusions typically form, where the presence of interferon-α-induced protein is associated with the formation of lupus inclusions which are, in turn, associated with immunodeficiency and autoimmune diseases such as AIDS and lupus erythematosus, or autoimmune conditions arising from interferon-α treatment of cancer.

For detection, the oligomers can be labeled with, for example, a radioactive isotope, biotin, an element opaque to X-rays, or a paramagnetic ion. Radioactive isotopes are commonly used and are well known to those skilled in the art. Representative examples include phosphorous-32, sulfur-35, indium-111, technetium-99m, and iodine-123. Biotin is a standard label which would allow detection of the biotin labeled oligomer with avidin. Paramagnetic ions are also commonly used and include, for example, chelated metal ions of chromium (III), manganese (II), and iron (III). When using such labels, the labeled DNA oligomer can be imaged using methods known to those skilled in the art. Such imaging methods include, but are not limited to, autoradiography, fluorography, X-ray, CAT scan, PET scan, NMRI, and fluoroscopy. Other suitable labels include enzymatic labels (horseradish peroxidase, alkaline phosphatase, etc.) and fluorescent labels (such as FITC, rhodamine, etc.).

As should be readily apparent to those skilled in the art, the DNA oligomers must selectively hybridize to nucleic acid molecules encoding interferon-α-induced protein in order to be useful as detecting agents. Therefore, the oligomers must either be of sufficient length to selectively hybridize to nucleic acid molecules encoding interferon-α-induced proteins, or the oligomers can be shorter molecules directed to consecutive nucleotides unique to the nucleic acid molecules encoding interferon-α-induced proteins. In either situation, the oligomers will selectively hybridize and detection assays will be accurate. Probes and primers as discussed above also need to have such selectivity to be most useful.

The invention further provides an antibody or fragment thereof specific for the interferon-α-induced protein encoded by the nucleic acid molecule of the subject invention. Antibodies of the subject invention include polyclonal antibodies and monoclonal antibodies capable of binding to the interferon-α-induced protein, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the Fab2, and the Fc fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell 1984 and St. Groth et al. 1980). Any animal (mouse, rabbit, etc.) which is known to produce antibodies can be immunized with the antigenic interferon-α-induced protein (or an antigenic fragment thereof). Methods for immunization are well known in the art. Such methods include subcutaneous or intraperitoneal injection of the enzyme. One skilled in the art will recognize that the amount of the enzyme used for immunization will vary based on the animal which is immunized, the antigenicity of the enzyme, and the site of injection.

The enzyme which is used as an immunogen may be modified or administered in an adjuvant in order to increase the enzyme's antigenicity. Methods of increasing the antigenicity of an enzyme (i.e., a protein) are well known in the art and include, but are not limited to, coupling the antigen with a heterologous protein (such as a globulin or beta-galactosidase) or including an adjuvant during immunization.

For monoclonal antibodies, spleen cells from the immunized animals are removed, fused with myeloma cells, such as SP2/O-Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al. 1988).

Hybridomas secreting the desired antibodies are cloned and the class and subclass are determined using procedures known in the art (Campbell 1984).

For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC, rhodamine, etc.), paramagnetic atoms, and the like. Procedures for accomplishing such labeling are well known in the art, such as the procedures described in, for example, Sternberger et al. 1970, Bayer et al. 1979, Engval et al. 1972, and Goding 1976.

The labeled antibodies or fragments thereof of the present invention can be used for in vitro, in vivo, and in situ assays to identify cells or tissues which express interferon-α-induced protein, to identify samples containing interferon-α-induced protein, or to detect the presence of interferon-α-induced protein in a sample. More particularly, the antibodies or fragments thereof can thus be used to detect the presence of interferon-α-induced protein in a sample, by contacting the sample with the antibody or fragment thereof. The antibody or fragment thereof binds to any interferon-α-induced protein present in the sample, forming a complex therewith. The complex can then be detected, thereby detecting the presence of interferon-α-induced protein in the sample. As will be readily apparent to those skilled in the art, such a method could also be used quantitatively to assess the amount of interferon-α-induced protein in a sample. Such a quantitative method could be especially useful in samples of cells wherein interferon-α is typically expressed or wherein lupus inclusions typically form, where the presence of interferon-α-induced protein is associated with the formation of lupus inclusions which are, in turn, associated with immunodeficiency and autoimmune diseases such as AIDS and lupus erythematosus, or autoimmune conditions arising from interferon-α treatment of cancer.

Fragments of the nucleic acid molecules encoding interferon-α-induced protein are also provided, and are best defined in the context of amino acid sequence relationships among members of the interferon-α-induced protein sequence family and information on the function of these proteins and specific interferon-α-induced protein domains. Antibodies prepared to a polypeptide encoded by conserved determinants would therefore be expected to be of use as reagents capable of detecting many members of the interferon-α-induced protein family. Such antibodies, if introduced into cells that express interferon-α-induced protein, would also be expected to modify the normal function of the interferon-α-induced and related proteins expressed in those cells. In contrast, antibodies can be prepared which are directed to an amino acid sequence that is less well conserved between the interferon-α-induced and related proteins. Antibodies prepared to the polypeptide encoded by this less well conserved fragment would therefore be expected to recognize selectively the interferon-α-induced protein from which the fragment was derived.

Since interferon-α-induced protein is associated with the presence of interferon-α, which, in turn, is associated with the formation of lupus inclusions, which are, in turn, associated with immunodeficiency and autoimmune diseases such as AIDS and lupus erythematosus, or autoimmune conditions arising from interferon-α treatment of cancer, there are numerous uses of the subject invention.

The present invention thus provides a method for detecting presence or prior existence of interferon-α in a sample. The method includes detecting presence of an interferon-α-induced protein in the sample. For example, the sample can be contacted with an antibody or fragment thereof, preferably labeled with a detectable marker, specific for an interferon-α-induced protein encoded by a nucleic acid molecule according to the subject invention. The antibody or fragment thereof binds to any interferon-α-induced protein present in said sample, forming a complex therewith. By detecting the complex, the presence of an interferon-α-induced protein in the sample is detected which, in turn, indicates the presence or past existence of interferon-α in the sample. Alternatively, the presence of an interferon-α-induced protein in the sample can be detected by contacting the sample with a DNA oligomer, preferably labeled with a detectable marker, capable of hybridizing to a nucleic acid molecule encoding an interferon-α-induced protein. The DNA oligomer hybridizes to any nucleic acid encoding the interferon-α-induced protein present in the sample, forming a complex therewith. Detection of the complex indicates the presence of a nucleic acid molecule encoding an interferon-α-induced protein which, in turn, indicates the presence or past existence of interferon-α in the sample.

The present invention also provides a method for detecting presence or prior existence of lupus inclusions in a sample. The method includes detecting presence of an interferon-α-induced protein in the sample. For example, the sample can be contacted with an antibody or fragment thereof, preferably labeled with a detectable marker, specific for an interferon-α-induced protein encoded by a nucleic acid molecule according to the subject invention. The antibody or fragment thereof binds to any interferon-α-induced protein present in said sample, forming a complex therewith. By detecting the complex, the presence of an interferon-α-induced protein in the sample is detected which, in turn, indicates the presence or past existence of lupus inclusions in the sample. Alternatively, the presence of an interferon-α-induced protein in the sample can be detected by contacting the sample with a DNA oligomer, preferably labeled with a detectable marker, capable of hybridizing to a nucleic acid molecule encoding an interferon-α-induced protein. The DNA oligomer hybridizes to any nucleic acid encoding the interferon-α-induced protein present in the sample, forming a complex therewith. Detection of the complex indicates the presence of a nucleic acid molecule encoding an interferon-α-induced protein which, in turn, indicates the presence or past existence of lupus inclusions in the sample.

The methods for detecting the presence of interferon-α-induced protein according to the present invention, such as by using DNA oligomers or antibodies and fragments thereof, can be used to diagnose autoimmune disease or the progression thereof in an individual. In one embodiment, the method comprises providing a sample of cells from an individual. The cells are selected to be cells in which interferon-α is typically expressed or wherein lupus inclusions typically form, such as T cells, B cells, endothelial cells and mononuclear cells. The method further comprises detecting presence of an interferon-α-induced protein in the sample, as described above. In a further embodiment, the method comprises inducing a sample of Raji or Daudi cells with a serum sample from the individual, and then detecting the presence of an interferon-α-induced protein in the induced Raji or Daudi cells sample. In either method, the presence of interferon-α-induced protein indicates the presence or past existence of interferon-α, lupus inclusions, or both in the sample, which, in turn, indicates the existence of an immunodeficiency or autoimmune disease in the individual, such as AIDS, lupus erythematosus, or disease resulting from interferon-α treatment, particularly prolonged interferon-α treatment, of cancer. These methods can also be used quantitatively to gauge the progression of immunodeficiency or autoimmune diseases, with the level of interferon-α-induced protein being indicative of a more advanced stage of disease.

As indicated above, levels of interferon-α-induced protein in a cell, such as a tumor cell, can be decreased by introducing an antisense or ribozyme construct into the cell. An antisense construct blocks translation of mRNA encoding interferon-α-induced protein into the interferon-α-induced protein. A ribozyme construct cleaves the mRNA encoding the interferon-α-induced protein, thus also preventing expression of functional interferon-α-induced protein. For in vivo decreasing of expression of interferon-α-induced protein, various gene therapy techniques can be utilized to introduce the antisense or ribozyme construct into the desired cell. The construct is preferably targeted to the desired cells (i.e., the tumor cells) by known methods.

Leader sequences can be employed for targeting of the interferon-α-induced nucleic acid molecule or protein to the desired cell or part of a cell. It should be readily apparent to those skilled in the art that a Met residue may need to be added to the amino terminal of the amino acid sequence of the mature interferon-α-induced protein (e.g. to SEQ ID NO: 2) or an ATG added to the 5' end of the nucleotide sequence (e.g. to SEQ ID NO: 1), in order to express the protein in some host cells. The Met version of the mature interferon-α-induced protein is thus specifically intended to be covered by reference to SEQ ID NO: 2. After expression of a leader/interferon-α-induced protein construct, the leader targets the interferon-α-induced protein within a cell before the leader peptide is cleaved from the mature interferon-α-induced protein.

The present invention is further illustrated by the following examples.

MATERIALS AND METHODS

Reagents

Biochemicals, enzymes, and antibody reagents were obtained from Sigma (St. Louis, Mo.) unless indicated otherwise.

IFN-α Induction of Raji cell p36 and LI

The human B lymphoblastoid cell line, Raji, is of Burkitt lymphoma origin (American Type Culture Collection, CCL 86). It was maintained in exponential growth as a suspension culture at densities between 0.025 and $1.0 \times 10^6$ cells/ml with <5% nonviable cells by resuspension in fresh RPMI 1640 medium, 10% fetal calf serum (Life Technologies, Inc., Gaithersburg, Md.), 100 units of penicillin, and 100 μg of streptomycin/ml. The doubling time of the cells was 18 h. Tissue culture flasks (Bellco Glass, Vineland, N.J.) were kept in a humidity-controlled incubator with a 5% $CO_2$ atmosphere at 37° C. Cell densities were determined in duplicate on a model F cytometer (Coulter Cytometry, Hialeah, Fla.), and the percentage of nonviable cells was determined by trypan blue exclusion.

The antiviral titer of the purified recombinant human IFN-α, pure recombinant human interferon-α A ("IFLrA") (Hoffman-LaRoche, Nutley, N.J.), was assayed on WISH cells challenged with vesicular stomatitis virus (Indiana strain) (Rubinstein et al. 1981) relative to the National Institutes of Health human interferon-α ("IFN-α") standard (GO23-901-527, National Institutes of Health, Bethesda, Md.). 1 unit/ml of interferon ("IFN") provides 50% protection for the WISH cell monolayers.

LI and p36 were induced by culturing Raji cells at an initial density of $0.063 \times 10^6$ cells/ml for 72 h with 100 units of IFLrA/ml. For the one experiment in which Raji cells were induced for only 2 h, the initial density was $0.25 \times 10^6$ cells/ml. As detailed below, cells were pelleted and overlaid with glutaraldehyde for electron microscopy, washed, and precipitated with trichloroacetic acid for one-or two-dimensional gel analyses or were used to prepare slides for immunofluorescence.

One and Two-dimensional Protein Maps

Two dimensional gels (isoelectric focusing (IEF) cylinders in the first dimension and SDS-PAGE slabs for the second dimension) were run according to the procedure described in O'Farrell 1975 and Rich and Gibbons 1989. The second dimension SDS-PAGE (12.5% acrylamide; Bio-Rad, Hercules, Calif.) by itself was used for one-dimensional protein maps (Laemmli 1970).

Samples for two-dimensional analyses were run on 3-mm inner diameter and 12-cm-long focusing cylinders. Cylinders were focused at 400 V for 16 h and then at 800 V for 1 h in a Polyanalyst apparatus (Haake, Inc., Paramus, N.J.) using 0.1M $H_3PO_4$ (anode) and 0.1M NaOH (cathode). Equilibrated cylinders (5 ml of 3% SDS (Bio-Rad), 6.2% β-mercaptoethanol, 62.5 mM Tris, pH 6.8, for 15 min at 4° C.) were attached to 0.75-mm-thick SDS slabs with a minimal volume of agarose. Low molecular weight markers (Pharmacia Biotechnology Inc., Piscataway, N.J.) were used for size calibration, and pH measurement was obtained with 0.5-cm-long slices of duplicate focused cylinders equilibrated in 1 ml of water. The vertical slab apparatus for SDS-PAGE (SE500, Hoefer Scientific Instruments, San Francisco, Calif.) was run at 10° C. and 110 V for 30 min, followed by 220 V, until the bromphenol blue dye marker reached the bottom of the slab (~3h). Slab, gels were stained with either Coomassie Brilliant Blue or silver (Dzandu et al. 1984).

Purification of p36

$500 \times 10^6$ IFLrA-induced Raji cells were resuspended in 40 ml of reticulocyte standard buffer ("RSB"), 0.1 mM phenylmethylsulfonyl fluoride, 0.1% Tween 40 at 4° C. (Rich 1995, Rich and Gibbons 1989, and Penman 1969). After 10 min on ice, the cells were gently vortexed until lysed. Nuclei were pelleted at 1500×g for 10 min. The cytoplasm-plus-membrane fraction (the nuclear supernatant) was further fractionated into a 100,000×g pellet and a soluble supernatant by centrifugation at 100,000×g for 1 h.

For fractionation on the Rotofor cell (Bio-Rad), the soluble supernatant was prepared in 2.06% ampholines (Pharmacia Biotechnology Inc.) (1:10 mixture of pH 3.5–10 and pH 5–7 ampholines), 3.18% Triton X-100, 0.07% SDS, 8.2M urea, 0.79% β-mercaptoethanol, 1.35 mM Tris-HCl, pH 7.4, 0.68 mM $MgCl_2$, 6.75 μg/ml pancreatic RNase, and 3.65 μg/ml pancreatic DNase (Rich and Gibbons 1989). Samples reached equilibrium (defined by a constant current for 30 min) by 5 h of electrofocusing at 4° C. and 12 watts of constant power, at which time the 20 fractions were harvested. The protein components in the Rotofor fractions were determined on two-dimensional gels that were stained by the silver method (Dzandu et al. 1984). Samples for two-dimensional gel analysis were prepared by combining 20 μl of a Rotofor fraction with 4 μl of the following mixture: 13.3% of a 1:10 mixture of pH 3.5–10 and pH 5–7 ampholines, 1.67% SDS, 35% Triton X-100, and 18.8% β-mercaptoethanol (Rich and Gibbons 1989).

Enriched p36 in Rotofor fractions was purified to homogeneity from 400-μl aliquots run on two-dimensional gels. The slab gels were lightly stained with 0.1% Coomassie Brilliant Blue and 10% methanol (without acetic acid) and destained in 10% methanol. Spots of pure p36 were cut out and equilibrated in sample buffer (5% β-mercaptoethanol, 50 mM Tris, pH 6.8, 1% SDS, 10% glycerol) for SDS-PAGE. Collected spots of pure p36 were concentrated into a single band of p36 on a 1.5-mm-thick one-dimensional SDS-PAGE slab (double the thickness of the two-dimensional gels), and electrotransferred onto either polyvinylidene difluoride ("PVDF") (Millipore, Bedford, Me.) or nitrocellulose (Bio-Rad) membrane with a Transphor apparatus (Hoefer Scientific Instruments, San Francisco, Calif.) (192 mM glycine, 20% methanol, 25 mM Tris, pH 8.3).

Microsequencing of p36 p36 on PVDF membrane was stained with Coomassie Brilliant Blue (0.1% in 10% methanol with destaining in 10% methanol) and subjected to direct microchemical sequencing (Hewick et al. 1981) and composition analysis. For amino acid analysis, the p36 on the PVDF membrane was hydrolyzed in constant boiling HCl at 110° C. for 22–24 h and analyzed for amino acids with a Beckman System Gold amino acid analyzer (Fullerton, Calif.).

For internal sequence determination, the band of p36 on nitrocellulose was stained with Ponceau S (Fluka, Ronkonkoma, N.Y.) (0.1% in 1% acetic acid and destained with 1% acetic acid), excised and further processed as described previously in Tempst et al. 1990, with modifications. Briefly, in situ proteolytic cleavage was done using 0.5 $\mu$g of trypsin (Promega, Madison, Wis.) in 25 $\mu$l of 100 mM $NH_4HCO_3$ (supplemented with 0.3% Tween 80) at 37° C. for 3 h. The resulting peptide mixture was reduced and S-alkylated with, respectively, 0.1% $\beta$-mercaptoethanol (Bio-Rad) and 0.3% 4-vinylpyridine (Aldrich, Milwaukee, Wis.) and fractionated by reversed phase HPLC. An enzyme blank was done on an equally sized strip of nitrocellulose HPLC solvents and system configuration were as described in Elicone et al. 1994 except that a 2.1 mm Vydac C4 (214TP54) column (The Separations Group, Hesperia, Calif.) was used with gradient elution at a flow rate of 100 $\mu$l/min. Fractions were collected by hand, kept on ice for the duration of the run, and then stored at −70° C. before analysis. Chemical sequencing of selected peptides was done using a model 477A instrument (Applied Biosystems, Foster City, Calif.) with "on-line" analysis (120 HPLC system with 2.1×220 mm phenylthiohydantoin C18 column, Applied Biosystems). Instruments and procedures were optimized for fmol level phenylthiohydantoin-derivative analysis as described previously (Tempst et al. 1994). Peptide sequences were compared with entries in various sequence data bases using the National Center for Biotechnology Information BLAST program (Altschul et al. 1990).

Rabbit Antipeptide Antibodies

Peptides of p36-derived sequence (T28, T37.8, T29, T48, and T50(½)) were prepared on an Applied Biosystems (Foster City, Calif.) 431A automated peptide synthesizer. N-(9-fluorenyl)methoxycarbonyl/tert-butyl ("Fmoc") chemistry (Plau and Brand 1988) was used with trifluoracetic acid cleavage in the presence of appropriate scavengers. The final product was lyophilized from aqueous buffer following extraction with organic solvent.

Glutaraldehyde at a final concentration of 1% was used to couple each of the synthetic peptides to the carrier proteins KLH and ovalbumin ("OVA") (Muller et al. 1986). Equimolar mixtures of these conjugates were used to immunize rabbits for the production of polyclonal antibodies reactive with p36. Preimmune serum samples were taken from each of the six rabbits. Two rabbits were inoculated with the mixture of six synthetic peptides, two with the mixtures of synthetic peptides conjugated to KLH, and two with the mixtures of synthetic peptides conjugated to OVA. Sera were decomplemented by heating at 56° C. for 30 min, sterile filtered (0.45 $\mu$m HAWP filters, Millipore, Bedford, Me.), and stored at −70° C.

Antibody titers were determined by enzyme-linked immunosorbent assay (van Regenmortel 1988). For test antigen, the synthetic peptides were conjugated to bovine serum albumin by 1-ethyl-3-(3-dimethylaminopropyl)-carbodiimide, which prevented cross-reactivity to KLH, OVA, and the linkages created by glutaraldehyde. Titers were determined relative to readings for a 1:100 dilution of the corresponding preimmune serum. Second antibody was goat anti-rabbit conjugated to alkaline phosphatase, and color development was with p-nitrophenyl phosphate. Plates were read on a BioTek (Winooski, Vt.) EL 340 BioKinetics Reader at a 405-nm wavelength.

Affinity purification (Harlow and Lane 1988) of rabbit antibodies (antiserum raised against KLH-conjugated peptides) reactive with p36 peptides was achieved on a column of CNBr-activated Sepharose 4B (Pharmacia Biotechnology Inc.) which was coupled to the mixture of the five synthetic peptides conjugated by 1-ethyl-3-(3-dimethylaminopropyl)-carbodiimide to bovine serum albumin. Bound p36-specific antibodies were eluted with 100 mM glycine, pH 3.0, into 1M Tris, pH 8.0. Aliquots were stored in 0.2% $NaN_3$ at −70° C.

Immunodetection of p36

Western analyses of p36 with the antipeptide antisera were performed on proteins electrotransferred onto PVDF membranes from one-dimensional SDS-PAGE gels. Membranes were blocked for 90 min with 5% nonfat dry milk, 1% normal goat serum in Tris-buffered saline (10 mM Tris, pH 7.4, 150 mM NaCl), 0.05% Tween 20, washed in Tris-buffered saline, 0.05% Tween 20, and incubated for 2–24 h with polyclonal anti-p36 antiserum. Bound antibodies were detected with alkaline phosphatase-conjugated goat anti-rabbit IgG (regular alkaline phosphatase) or with biotinylated goat anti-rabbit IgG followed by a conjugate of streptavidin-biotinylated alkaline phosphatase (amplified alkaline phosphatase). In both cases, 5-bromo-4-chloro-3-indolyl phosphate and nitro blue tetrazolium were used as substrate and color development reagents.

For quantitative immunoprecipitation, p36 in the 100,000×g supernatant from $3 \times 10^6$ IFLrA-induced Raji cells was first precipitated with trichloracetic acid (7.5%), extracted with ethyl ether, solubilized (21 $\mu$l of 0.1N NaOH), neutralized (20 $\mu$l of 0.1N HCl plus 75 $\mu$l of 0.1M Tris, pH 7.0) and brought to 150 $\mu$l with $H_2O$. It was then reacted overnight with 20 $\mu$l of antipeptide serum and with 50 $\mu$l of Pro-A-Sepharose (Pharmacia Biotechnology Inc.) beads for an additional hour. The beads were pelleted and washed. The p36 adsorbed and not adsorbed to the beads was determined by Western analysis.

For immunofluorescence, glass microscope slides of Raji cell suspensions were prepared on a Cytospin (Shandon Scientific Ltd., Cheshire, UK) (400×g for 5 min), air-dried, fixed for 10 min in a 50—50 mixture of methanol and acetone, and washed in PBS just prior to use. The slides were incubated for 1 h with antibodies of either affinity-purified rabbit anti-p36 or mouse monoclonal-anti-protein-disulfide isomerase that were diluted 50-fold in 2% bovine serum albumin, 0.1% saponin (Baker Inc., Phillipsburg, N.J.), PBS. The slides were washed in this antibody buffer and reincubated with the appropriate goat second antibody (Cappel, Organon Teknika Corp., West Chester, Pa.) (fluorescein-labeled to detect p36 and rhodamine-labeled to detect protein-disulfide isomerase). The slides were again washed, mounted in Vectashield H-1000 medium (Vector Laboratories, Burlingame, Calif.), examined in a Nikon (Melville, N.Y.) Optiphot microscope equipped with epifluorescence optics and a Nikon 100 x oil objective lens, and photographed on Ilford-XP2 (Ilford Limited, Cheshire, UK) 400 ASA film.

Electron Microscopy and Enumeration of LI

Cell samples were fixed in 3% glutaraldehyde (Sorensen's phosphate buffer, pH 7.4), post-fixed in osmium tetroxide, dehydrated in graded ethanol, and embedded in Epon (Rich 1981). Thin (0.1 µm) sections were stained with uranyl acetate and then with lead citrate, and examined at 10,000 x on a Philips 301 electron microscope (Philips Electronic Instruments Company, Mahwah, N.J.).

LI frequencies are based on a binomial model (Rich 1981). The ratio of the mean diameter of LI to the whole cells is the probability ("d") of observing an LI in a random thin section of a given cell that contains an LI. Factoring in the probability that an LI exists in the cell ("p") gives a probability of observing LI in a cell population ("p*"), or p*=dp. For each sample, 400 independent cell sections were examined. Thin sections separated by greater than the 20-µm diameter of the cells were used to attain random sampling. A 10% frequency (p*) (40 out of 400 independent cell sections) is consistent with one 20-µm diameter LI (p=1) per cell of a 20 µm diameter (d=2.0 µm/20 µm=10%). The corresponding 95% confidence interval of LI is 7–13% (Rich 1981).

cDNA sequencing

The complete p36 cDNA sequence was obtained in three steps. The generation of a PCR fragment that coded for an internal sequence of the p36 protein, the remainder of the 3' cDNA using 3' RACE (rapid amplification of cDNA ends), and finally the remainder of the 5' cDNA by 5' RACE. In all three cases, the cDNA molecules obtained from the PCR reactions were isolated from agarose gels, cloned into the vector PCRII (Invitrogen, San Diego, Calif.), and DNA sequenced using the Sequenase Version 2.0 DNA Sequencing Kit (United States Biochemical, Cleveland, Ohio). To ensure accuracy of the DNA sequences, several clones were sequenced on both DNA strands. For the few base discrepancies detected, a consensus sequence was reported according to the majority of clones examined.

Total RNA was isolated from 72 hour interferon-α induced Raji cells and reverse transcribed into cDNA using an oligo dT primer. This cDNA preparation was used in a PCR reaction with degenerate primers that corresponded to the p36 amino acid sequence for the trypsin fragments $T_{501/2}$ (antisense) and $T_{48}$ (sense). A 560 bp product was obtained that encoded not only the 2 peptides upon which the degenerate primers were designed, but 3 of the remaining 4 tryptic fragments of p36 that had been microsequenced. The missing 3' sequence was obtained from the same preparation of cDNA in a PCR reaction with oligo dT and a nondegenerate sense oligo designed from the internal DNA sequence of the 560 bp PCR product. The missing 5' sequence was obtained from the same preparation of total RNA, but it was reverse transcribed using a nondegenerate antisense oligo designed from the internal DNA sequence of the 560 bp PCR product. This approach should generate cDNAs from only p36 mRNAs because of the use of the p36 specific antisense oligo in the reverse transcription reaction as opposed to the earlier use of oligo dT which produces cDNA from all of the mRNAs. The mRNA that formed RNA-DNA heteroduplex molecules in this preparation was destroyed with RNAase H, and a homopolymericC (poly C) tail was added to these cDNA molecules by TdT (terminal deoxynucleotidyl transferase) and dCTP. PCR amplification of p36 specific cDNAs was achieved using the anchor primer (BRL, lot no. DM 4102) and a nested p36 specific primer. A second set of nested primers were used (located 5' of the p36 cDNA end and 3' of the already obtained partial sequence of p36 cDNA) in a reamplification reaction to produce a DNA band on agarose gels to provide the remaining 5' sequence of p36 cDNA. This most 5' region contained the coding sequence for the sixth p36 trypsin fragment.

p36's full length protein sequence was obtained by translation of the open reading portion of p36's cDNA sequence into the corresponding protein using the GCG (Genetics Computer Group, Madison, Wis.) module TRANSLATE.

A discussion relating to the isolation and characterization of p36 can be found in Rich et al. 1996.

EXAMPLE 1

IFN-α Induction of LI and p36 in Raji Cells

Raji cells were maintained in an exponentially growing culture with a doubling time of 18 h. No LI were detected in 400 random thin sections of these cells. Growth of these cells in the presence of 100 units/ml of IFLrA for 72 h had no effect on their doubling time. These cells developed LI at a frequency of 11.75% (47 LI were detected in 400 random thin sections of Raji cells) by 72 h. This frequency translated (Rich 1981) into a single LI of an average 2.35-µm diameter/ cell of 20 µm average diameter (0.1175×20 µm). LI in these cells, stained with uranyl acetate and then with lead citrate and examined in a Philips 301 electron microscope, appeared as a complex of microtubular elements 20–28 nm in diameter that localized in the lumen of the endoplasmic reticulum. Earlier work (Rich 1981) with untreated Raji cells failed to detect any LI in 15,000 random thin sections or less than one LI of an average 2.5-µm diameter/500 cells of an average diameter of 20 µm.

Two-dimensional analyses of 400-µg amounts of protein from untreated and IFLrA-induced Raji cells failed to reveal any differences resulting from the IFLrA treatment when these gels were stained with Coomassie Brilliant Blue. Silver staining of gels with IFLrA-induced Raji cells made p36 apparent. This trace protein, having an estimated molecular weight of 36 kDa and an isoelectric point of 5.6, was greatly intensified by silver staining when compared with neighboring proteins.

EXAMPLE 2

Purification and Microsequencing of p36

A suspension of nuclei and cytoplasm plus membrane was prepared from IFLrA-induced Raji cells by gentle vortexing in the low ionic strength buffer RSB/Tween 40. Nuclei, cytoplasm plus membrane, 100,000 x g pellet, and 100, 000×g supernatant fractions were prepared by differential centrifugation of this suspension. p36 was detected only in the cytoplasm plus membrane and the 100,000×g supernatant fractions. The 100,000×g supernatant contained 38% of the total cell protein. Rotofor fractionation of this soluble supernatant prepared from 50×10$^6$ IFLrA-induced cells typically focused p36 among fractions 11, 12, and 13 with isoelectric points of 5.6, 5.7, and 5.8, respectively. p36 in these fractions focused near the middle of the isoelectric focussing ("IEF") cylinders used in two-dimensional gels to purify p36 to homogeneity.

Acid hydrolysis and amino acid analysis showed that 89 pmol of pure p36 was obtained from 2,000×10$^6$ IFLrA-induced Raji cells. This amount of sample required 90 IEF cylinders to be run on 30 SDS slabs (i.e. three central portions of IEF cylinders applied to a single SDS slab). The 90 spots of p36 were cut out, collected in SDS sample buffer, and concentrated into a single band on an SDS slab of double thickness, and electrotransferred to PVDF or nitrocellulose membranes.

Direct microsequencing of 89 pmol of p36 did not yield any result, indicating the likelihood of a blocked N terminus. Tryptic digestion of approximately 100 pmol of nitrocellulose bound p36 was then carried out, giving peptides that were fractionated by microbore-HPLC and successfully sequenced (Table I).

Computer searches of these six p36 peptides, which represent 31.3% of the entire amino acid sequence of p36 (93 amino acids/297 amino acids in p36), provided either no matches or ones without any statistical significance (Table I) with all five of the protein data bases contained in the network service BLAST (Altschul et al. 1990) (Brookhaven Protein Data Bank, Kabat Sequences of Proteins of Immunological Interest, PIR, Swiss-Prot, and Swiss-Prot Weekly Update). On the basis of these findings, it was concluded that p36 is a new IFN-α-induced protein.

TABLE I

Amino acid sequences and protein database analyses of the p36 trypsin peptides

| Trypsin Fragment | Microsequence | Smallest sum probability (p)[a] |
|---|---|---|
| T42 | SEQ ID NO:3: LQIITDFDMTLSK | NS[b] |
| T28 | SEQ ID NO:4: MADGVANVEHILK | NS |
| T37.8 | SEQ ID NO:5: VVSNFMDFDETGVLK | NS |
| T29 | SEQ ID NO:6: DNSNIILLGDSQGDLR | NS |
| T48 | SEQ ID NO:7: YYAIEVDPVLTVEQKYP | NS |
| T50 (1/2) | SEQ ID NO:8: YMDSYDIVLVQDESLEVAR | NS |

[a]Computations were performed at the National Center for Biotechnology Information using the BLAST network service (Altschul et al. 1990). p is the probability of finding a score this high or higher in a random database of the size searched. The databases searched were Brookhaven Protein Data Bank, Kabat Sequences of Proteins of Immunological Interest, PIR, Swiss-Prot, and Swiss-Prot Weekly Update.
[b]All of the p values obtained were greater than 0.05 (the lowest p value was 0.089 for T37.8 with Kabat Sequences of Proteins of Immunological Interest), the usual standard for statistical significance. However, because all six peptides were searched, and in all five of the databases, the p value for significance here is even lower (0.05/30) (Feller 1952), owing to adjustment for multiple comparisons.

EXAMPLE 3

Immunolocation of p36 in Raji Cell Fractions

Six rabbits (Flemish giant Chinchilla Cross, Nys-{SG}) that were immunized with the mixture of synthetic peptides formulated to match the p36 trypsin fragments T28, T37.8, T29, T48, and T50(½) made high titered antisera that were specific for p36. The 80 amino acids in these five peptides represent approximately 26.9% of the amino acids in the entire p36 (80 amino acids/297 amino acids for p36). Enzyme-linked immunosorbent assay-determined antibody titers of 9600 and 25,600 were obtained for the two rabbits that were inoculated with unconjugated peptides. The two rabbits that were injected with peptides conjugated to OVA produced antibody titers of 51,200 and 102,400. Both rabbits that were injected with peptides conjugated to KLH produced antibody titers of 102,400. The animals immunized with unconjugated peptides not only produced antibodies that were of lower titer, but their response to make antibodies was much delayed when compared with the animals that were injected with the conjugated peptides.

Reaction of these antibodies with p36 in Raji cells was assayed by Western blots. Cell fractions were prepared by differential centrifugation of Raji cell extracts prepared with RSB made 0.1% in Tween 40. The soluble supernatant and the insoluble membrane fraction were prepared by centrifuging the cytoplasm-plus-membrane fraction at 100,000×g for 1 h. The samples were run on a 12.5% SDS-PAGE, electrotransferred to a PVDF membrane, and reacted with an antiserum prepared against the synthetic peptides that were conjugated to KLH. The six rabbit antisera reacted specifically with p36 in induced Raji cells when tested at a 1:100 dilution and developed with alkaline phosphatase, with no reaction occurring at this molecular weight location in the untreated cells. Additional nonspecific staining was common to both uninduced and induced Raji cells. The nonspecific bands were unique for each rabbit, and they occurred both with preimmune serum as well as the serum that contained high antibody titers.

p36 and nonspecific bands were stained in whole cell samples of IFLrA-induced Raji cells while only the nonspecific bands were stained in the untreated cells (1:1000 dilution). p36 was detected in the nuclear supernatant, and the supernatant of the 100,000×g pellet, but not in the nuclear, or 100,000×g, pellets. p36 was not detected in any of the corresponding control fractions. Equal loading of protein in corresponding sample wells was demonstrated by equal staining of the nonspecific bands. As indicated by these results, IFN-α-induced p36 was located solely in the cytoplasm.

In addition to p36 in the cytoplasm of 72-h IFLrA-induced Raji cells, these cells also secreted sufficient p36 by an additional 24 h of culturing in serum-free medium (containing 100 units/ml of IFLrA) for its detection by Western blotting. The amount of p36 applied was obtained from $1 \times 10^6$ Raji cells. The size of secreted p36 was the same as intracellular p36, and the portion of p36 that was secreted was estimated to be 10% of that present in $1 \times 10^6$ cells. No p36 was seen in the corresponding serum-free medium from untreated Raji cells. These results showed that untreated Raji cells neither produced nor secreted p36, and that any post-translational changes that may accompany p36 secretion from IFLrA-induced cells did not significantly alter its size according to its migration in SDS gels.

EXAMPLE 4

Specificity of p36 Antipeptide Antibodies

Western analysis showed that p36 in the 100,000×g supernatant fraction was poorly precipitated by overnight reaction with p36 antipeptide antiserum and protein A beads in comparison with the same amount of p36 applied directly to an SDS slab. Near complete immunoprecipitation of p36 in solution was accomplished by denaturation of the 100,000×g supernatant sample by trichloroacetic acid precipitation and resolubilization. A diminished reaction with antiserum was achieved in 8M urea. In agreement with these results, only a trace amount of p36 denatured by trichloroacetic acid remained unbound to the antibodies, while, without denaturation, an estimated amount greater than 80% remained unbound. These results suggest that the epitopes recognized by the antipeptide antibodies are folded into the interior of the native protein.

Amplified alkaline phosphatase development of Western assays of the 100,000×g supernatant fractions provided a clear specificity for p36. No background staining occurred with the corresponding control fraction between antiserum dilutions of 1:50,000 and 1:1.5×10⁶ in 0.2 and 0.5×10⁶ IFLrA-induced Raji cells. In IFLrA-induced cells, p36 was increased at least 400 times as measured by the detection of p36 out to a 400-fold dilution. Specificity of the antiserum reaction with p36 was shown by its blockage upon preincubation with the mixture of unconjugated synthetic peptides and the absence of an effect from preincubation with myoglobin. Cell samples reacted only with the streptavidin-biotinylated alkaline phosphatase complex stained the high molecular weight band of biotin that was endogenous to Raji cells.

EXAMPLE 5

Localization of p36 in the Endoplasmic Reticulum

Immunofluorescence microscopy confirmed that p36 was present only in the 72-hour IFLrA-induced Raji cells. p36 antibodies, purified on an affinity column of bound p36 synthetic peptides, demonstrated p36 specific immunofluorescence of IFLrA-induced Raji cells when they were fixed and permeabilized with methanol and acetone, and the antibodies were applied in saponin buffer.

The location of p36 in the cytoplasm, and the particular region of the cytoplasm in which p36 localized, was determined by double immunofluorescence with anti-p36 and a monoclonal antibody to protein-disulfide isomerase; protein-disulfide isomerase is an ER-resident protein (Noiva and Lennarz 1992 and Quemeneur et al. 1994). Antibodies to protein-disulfide isomerase stained (rhodamine-labeled second antibody) the same cytoplasmic region of untreated and IFLrA-induced Raji cells. This showed that the distribution of protein-disulfide isomerase was not altered by IFLrA treatment. Micrographs of the same IFLrA-treated cells showed the colocalization of p36 in the same cytoplasmic region as protein-disulfide isomerase, the ER, and the location of the cytoplasm and nuclei in phase contrast. These results showed that p36 in IFLrA-induced Raji cells was restricted to the ER, the same region in which LI formed.

Immunofluorescence microscopy also showed that p36 was just detectable by 45 min of IFLrA treatment of a culture of Raji cells in exponential growth with a doubling time of 18 h. If p36 expression was cell cycle-dependent, then only a proportion of the cells at 2 h of induction would stain for p36, like a mixture of induced and uninduced Raji cells. If p36 expression was independent of cell cycle stages, then all of the cells would stain for p36, similar to the pattern seen for 72-h IFLrA-induced Raji cells, but with a lesser intensity of fluorescence. Immunofluorescent staining showed that p36 was being expressed by all of these cells, and with a lesser intensity than Raji cells that were induced for 72 h with IFLrA. These results indicate that p36 expression was not restricted to a single cell cycle phase.

EXAMPLE 6

Amino Acid and Nucleotide Sequences

The amino acid sequence of the p36 protein is shown in SEQ ID NO: 2. This sequence includes the N-terminal methionine which may be removed for expression in some host cells such as mammalian cells.

The nucleotide sequence of the p36 protein is shown in SEQ ID NO: 1. This sequence represents the open reading frame (ORF) of p36. SEQ ID NO: 9 shows the p36 nucleotide sequence including the 5' untranslated region (nucleotides 1–53 of SEQ ID NO: 9), the ORF (nucleotides 54 to 944 of SEQ ID NO: 9), and the 3' untranslated region (nucleotides 945–1541 of SEQ ID NO: 9).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

LIST OF REFERENCES CITED

Altschul, S. F., et al., *J. Mol. Biol.* 215:403–410 (1990).
Balass, M., et al., *Proc. Natl. Acad. Sci. USA* 90:10638–10642 (1993).
Baron, S., et al., *Interferon: Principles and Medical Applications,* pp. 1–15, The University of Texas Medical Branch, Galveston, Tex. (1992).
Bayer, E. A., et al., *Meth. Enzym.* 62:308 (1979).
Beresini, M. H., et al., *J. Immunol.* 140:485–493 (1988).
Bevan, P., et al., *Trends in Biotechnology* 13:115–121 (1995).
Bordo, D. and Argos, P., *J. Mol. Biol.* 217:721–729 (1991).
Campbell, A. M., *Monoclonal Antibody Technology: Laboratory Techniques in Biochemistry and Molecular Biology,* Elsevier Science Publishers, Amsterdam, The Netherlands (1984).
Capecchi, M., *Cell* 22:479–488 (1980).
Chrisey, L., et al., *Antisense Research and Development* 1:57–63 (1991).
Christian, R. B., et al., *J. Mol. Biol.* 227:711–718 (1992).
Christoffersen, R. E. and Marr, J. J., *Journal of Medicinal Chemistry* 38:2023–2037 (1995).
Cwirla, S. E., et al., *Proc. Natl. Acad. Sci. USA* 87:6378–6382 (1990).
De Stefano, E., et al., *J. Infect. Dis.* 146:451–459 (1982).
Dianzani, F., *Interferon: Principles and Medical Applications* pp. 409–416, The University of Texas Medical Branch, Galveston, Tex. (1992).
Dron, M. and Torey, M. G., *Iterferon: Principles and Medical Applications,* pp. 33–45, The University of Texas Medical Branch, Galveston, Tex. (1992).
Dzandu, J. K., et al., *Proc. Natl. Acad. Sci. U.S.A.* 81:1733–1737 (1984).
Elicone, C., et al., *J. Chromatogr.* 676:121–137 (1994).
Engval, E., et al., *Immunol* 109:129 (1972).
Feller, W., *An Introduction to Probability Theory and Its Applications,* pp. 75, John Wiley and Sons, Inc., N.Y. (1952).
Feremans, W. W., et al., *J. Clin. Pathol.* 41:62–71 (1988).
French, S. and Robson, B., *J. Molecular Evolution* 19:171–175 (1983).
Goding, J. W., *J. Immunol. Meth.* 13:215 (1976).
Gustafsson, A., et al., *J. Immunol.* 129:1952–1959 (1982).
Gutterman, J. U., *Proc. Natl. Acad. Sci. U.S.A.* 91:1198–1205 (1994).
Gyorkey, F., et al., *N. Engl. J. Med.* 280:333 (1969).
Han, L., et al., *Proc. Natl. Acad. Sci. USA* 88:4313–4317 (1991).
Harlow, E., and Lane, D., *Antibodies, a Laboratory Manual,* pp. 145–175, Cold Spring Harbor Laboratory, Cold Spring Harbor, N.Y. (1988).
Heim, M. H., et al., *Science* 267:1347–1349 (1995).
Henco, K., et al., *J. Mol. Biol.* 185:227–260 (1985).
Hewick, R. M., et al.,*J. Biol. Chem.* 256:7990–7997 (1981).
Hobart, M. J., et al., *Proc. R. Soc. London B* 252:157–162 (1993).
Hooper, W. C., *Blood, Blood Products, and HIV* 2nd Ed., pp. 101–116, Chapman & Hall Medical, N.Y. (1994).

Ihle, J. N., and Kerr, I. M., *Trends Genet.* 19:222–227 (1995).

Innis, et al., *PCR Protocols,* Academic Press, San Diego, Calif. (1990).

Issacs, A., and Lindenmann, J., *Proc. R. Soc. London* 147:258–267 (1957).

Klein, T. M., et al., *Nature* 327:70–73 (1987).

Laemmli, U. K., *Nature* 227:680–685 (1970).

LaRocca, D., et al., *Hybridoma* 11:191–201 (1992).

Leanderson, T., et al., *EMBO J.* 1:1505–1511 (1982).

Lutz, et al., *Exp. Cell. Res.* 175:109–124 (1988).

Mannino, R. J. and Gould-Fogerite, S., *BioTechniques* 6:682–690 (1988).

Miller, L. K., *Bioassays* 11:91–95 (1989).

Muller, S., et al., *Mol. Immunol.* 23:593–601 (1986).

Noiva, R., and Lennarz, W. J., *J. Biol. Chem.* 267:3553–3556 (1992).

O'Connor, B., et al., *Cancer Chemother. Pharmacol.* 34:225–229 (1994).

O'Farrell, P. H., *J. Biol. Chem.* 250:4007–4021 (1975).

Orenstein, J. M., et al., *Am. J. Clin. Pathol.* 84:603–609 (1985).

Parmley, S. F. and Smith, G. P., *Gene* 73:305–318 (1988).

Paul, W. E., and Seder, R. A., *Cell* 76:241–251 (1994).

Penman, S., *Fundamental Techniques in Virology,* pp. 35–48, Academic Press, N.Y. (1969).

Pestka, S., et al., *Annu. Rev. Biochem.* 56:727–777 (1987).

Plaue, S., and Brand, J. P., *Laboratory Techniques in Biochemistry and Molecular Biology* Vol. 19, pp. 41–94, Elsevier, N.Y. (1988).

Preble, O. T., et al., *Science* 216:429–431 (1982).

Quemeneur, E., et al., *J. Biol. Chem.* 269:5485–5488 (1994).

Rhee, M., et al., *Pharmacol.* 2:97–101 (1995).

Rhee, M. S., et al., *Cellular Pharmacol.* 2:289–292 (1995).

Rich, S. A., *J. Clin. Invest.* 95:219–226 (1995).

Rich, S. A., *Science* 213:772–775 (1981).

Rich, S. A., and Gibbons, W. E., *Arthritis & Rheum.* 33:1420–1425 (1990).

Rich, S. A., and Gibbons, W. E., *Technique (Philadelphia)* 1:196–203 (1989).

Rich, S. A., and Owens, T. R., *J. Interferon Res.* 4:335–345 (1984).

Rich, S. A., et al., *Arthritis Rheum.* 29:501–507 (1986).

Rich, S. A., et al., *J. Biol. Chem.* 271:1118–1126 (1996).

Rich, S. A., et al., *J. Struct. Biol.* 108:25–34 (1992).

Rich, S. A., et al., *Lancet* i:127—127 (1983).

Rossi, J. J., et al., *AIDS Research and Human Retroviruses* 8(2):183–189 (1992).

Rossi, J. J., *British Medical Bulletin* 51(1):217–225 (1995).

Rubinstein, S., et al., *J. Virol.* 37:755–758 (1981).

Sambrook et al., *Molecular Cloning: A Laboratory Manual,* 2d Edition, Cold Spring Harbor Laboratory Press, Cold Spring Harbor, N.Y. (1989).

Schattner, A., *Clin. Immunol. Immunopathol.* 70:177–189 (1994).

Scott, J. K., *Trends in Biochem. Sci.* 17:241–245 (1992).

Scott, J. K. and Smith, G. P., *Science* 249:386–390 (1990).

Sen, G. C., and Ransohoff, R. M., *Adv. Virus Res.* 42:57–102 (1993).

Sepetov, N. F., et al., *Proc. Natl. Acad. Sci. USA* 92:5426–5430 (1995).

Shigekawa, K. and Dower, W. J., *BioTechniques* 6:742–751 (1988).

Sidhu, G. S., et al., *Human Pathol.* 16:377–386 (1985).

Skurkovich, S., et al., *Med. Hypotheses* 41:177–185 (1993).

Smith, G. P. and Scott, J. K., *Methods in Enzymology* 217:228–257 (1993).

Staeheli, P., *Adv. Virus Res.* 38:147–200 (1990).

Sternberger, L. A., et al., *J Histochem. Cytochem.* 18:315 (1970).

Stewart, T. A., et al., *Science* 260:1942–1946 (1993).

St. Groth, et al., *J. Immunol. Methods* 35:1–21 (1980).

Taylor, W. R., *J. Theor. Biol.* 119:205–218 (1986).

Tempst, P., et al., *Electrophoresis* 11:537–553 (1990).

Tempst, P., et al., *Methods Companion Methods Enzymol.* 6:248–261 (1994).

Tolaymat, A., et al., *J. Pediat,* 120:429–432 (1992).

van Regenmortel, M. H., *Laboratory Techniques in Biochemistry and Molecular Biology* Vol. 19, pp. 145–176, Elsevier, N.Y. (1988).

Wandl, U. B., et al., *Clin. Immunol. Immunopathol.* 65:70–74 (1992).

Webber, G., et al., *J. Med. Chem.* 36:733–736 (1993).

What is claimed is:

1. An isolated nucleic acid molecule encoding a human interferon-α-induced protein wherein said nucleic acid molecule encodes an amino acid sequence as shown in SEQ ID NO: 2.

2. The isolated nucleic acid molecule of claim 1 wherein said nucleic acid is deoxyribonucleic acid.

3. The isolated nucleic acid molecule of claim 2 wherein said deoxyribonucleic acid is cDNA.

4. The isolated nucleic acid molecule of claim 1 wherein said nucleic acid is ribonucleic acid.

5. The isolated nucleic acid molecule of claim 4 wherein said ribonucleic acid is mRNA.

6. A recombinant cell comprising the nucleic acid molecule of claim 1.

7. An expression vector comprising the nucleic acid molecule of claim 1.

8. The expression vector of claim 7 wherein said expression vector is selected from the group consisting of a plasmid and a virus.

9. A cell comprising the expression vector of claim 7.

10. A method of producing an interferon-α-induced protein, said method comprising:
   introducing the nucleic acid molecule of claim 1 into a cell; and
   allowing said cell to express said nucleic acid molecule resulting in the production of the interferon-α-induced protein in said cell.

* * * * *